United States Patent
D'Amelio, Sr. et al.

(10) Patent No.: US 7,658,955 B2
(45) Date of Patent: Feb. 9, 2010

(54) *PUERARIA CANDOLLEI* VAR. *MIRIFICA* A SHAW. & SUVAT. EXTRACT

(75) Inventors: Frank S. D'Amelio, Sr., Huntington, NY (US); Youssef W. Mirhom, Huntington Station, NY (US)

(73) Assignee: Bio-Botanica, Inc., Hauppauge, NY (US)

( * ) Notice: Subject to any disclaimer, the term of this patent is extended or adjusted under 35 U.S.C. 154(b) by 0 days.

(21) Appl. No.: 11/070,269

(22) Filed: Mar. 3, 2005

(65) Prior Publication Data

US 2005/0196475 A1    Sep. 8, 2005

Related U.S. Application Data

(60) Provisional application No. 60/549,155, filed on Mar. 3, 2004.

(51) Int. Cl.
*A61K 36/00* (2006.01)
(52) U.S. Cl. .................................................... 424/725
(58) Field of Classification Search ................. 424/757
See application file for complete search history.

(56) References Cited

U.S. PATENT DOCUMENTS

| 5,679,806 | A | * | 10/1997 | Zheng et al. | 549/403 |
| 6,352,685 | B2 | * | 3/2002 | Hoshino et al. | 424/59 |
| 6,673,377 | B1 | * | 1/2004 | Cherdshewasart | 424/725 |
| 2002/0058062 | A1 | * | 5/2002 | Bombardelli et al. | 424/456 |

FOREIGN PATENT DOCUMENTS

| GB | 785987 A | * | 11/1957 |
| WO | WO 0115718 A1 | * | 3/2001 |

OTHER PUBLICATIONS http://www.ers.usda.gov/publications/arei/ah712/AH7123-3.PDF.*
Chansakaow, S et al. Identification of Deoxymiroestrol as the Actual Rejuvinating Principle of "Kwao Keur", *Pueraria mirifica*. The Known Miroestrol May Be an Aritifact J. Nat. Prod. Feb. 2000, vol. 63. No. 2, pp. 173-175.*
http://www.ildis.org/LegumeWeb/6.00/taxa/16077.shtml.*
http://www.adamhawa.com/pueraria_mirifica.htm.*
http://pgrc3.agr.ca/cgi-bin/npgs/html/taxon.pl?317850.*
Lo TC, Baird MHI and Hanson C. 'Handbook of Solvent Extraction'. John Wiley & Sons, 1983. Chapter 20: Liquid-Liquid Extraction in the Food Industry. pp. 593-603.*
(U1) Murphy PA, Barua K and Hauck CC. 'Solvent Extraction Selection in the Determination of Isoflavones in Soy Foods'. Journal of Chromatography B. vol. 777 (2002) 129-138.*

* cited by examiner

*Primary Examiner*—Christopher R Tate
*Assistant Examiner*—Amy L Clark
(74) *Attorney, Agent, or Firm*—Roylance, Abrams, Berdo & Goodman, L.L.P.

(57) ABSTRACT

An extract is derived from *Pueraria candollei* var. *mirifica* A Shaw. & Suvat. for topical and internal use in treating a subject. The extract is obtained by a sequential extraction process using a sequence of different solvents or mixtures of solvents in varying ratios and thereafter combining the liquid extracts. The liquid extract is then evaporated to dryness to obtain the extract. The extract is used in a topical composition that when applied to the skin reduces wrinkles without eye irritation.

17 Claims, No Drawings

PUERARIA CANDOLLEI VAR. MIRIFICA A SHAW. & SUVAT. EXTRACT

CROSS-REFERENCE TO RELATED APPLICATION

This application claims the benefit under 35 U.S.C. §119(e) of prior provisional application No. 60/549,155, filed Mar. 3, 2004, which is hereby incorporated by reference in its entirety.

FIELD OF THE INVENTION

The present invention is directed to a process for obtaining an extract of *Pueraria candollei* var. *mirifica* A Shaw. & Suvat. and to the extract obtained by the extraction process. The invention is also directed to an extract of *Pueraria candollei* var. *mirifica* A Shaw. & Suvat. that contains miroestrol with lesser amounts of isomers and derivatives of deoxymiroestrol, genistein, diadzin, puerarin, genistin and diadzein in effective amounts for topical and internal use.

BACKGROUND OF THE INVENTION

For more than 500 years, people in South East Asia have been using the root of "White Kwao Krua" for its profound anti-aging properties. This root has been identified as *Pueraria candollei* var. *mirifica* Airy Shaw et Suvat, which belongs to the family Papilionaceae (Leguminosae).

Folklore states that the root is a "fountain of youth" for aged men and women. It serves as an anti-wrinkle agent for aged and wrinkled skin, darkens white hair and increases hair growth, alleviates cataract problems, helps with memory loss, increases energy and vigor, blood circulation, appetite and sleep disorders.

The name *mirifica* in Latin means "miracle". There are more than 13 related, identified species of *Pueraria* with similar tuberous roots. They can be differentiated by the taxonomical characteristics of leaf, flower, inflorescence, fruit and covering trichomes. The only species with distinct estrogenic activity was found to be *Pueraria candollei* var. *mirifica* A. Shaw. & Suvat. (hereinafter "*Pueraria mirifica* or *P. mirifica*). Even the taxonomically similar species *Pueraria candollei* Graph. Ex. Benth. does not contain any measurable amount of Miroestrol and also lesser amounts of isoflavonoids.

Therefore, the properly identified roots are collected and their Phytoestrogens HPLC fingerprints authenticated before any further processing. For best results, the location, age of plant (2-4 years), atmospheric conditions (no rain), drying process and storage conditions are carefully monitored.

In "Anusarnsoondhorn, L. (1931) The Ingredient of *Pueraria* Tuberous Root", translated from Siamese, it is mentioned that the use of this root will make the skin smooth like a six year old child and allow you to live 1,000 years and prevent suffering from parasites, while also enhancing memory. Wanadorn, P. W., in "A Reputed Rejuvenator", *J. Siam Society, Natural History Supp.*, 8, 337 (1931), wrote "The ability of *P. mirifica* to produce a soft, youthful skin, and to turn White hair black, is stressed".

SUMMARY OF THE INVENTION

The present invention is directed to a process for obtaining an extract of *Pueraria candollei* var. *mirifica* A Shaw. & Suvat., the extract obtained by the process and the composition containing the extract. The invention is further directed to methods of treating a subject by administering topically or internally.

One aspect of the invention is to provide a process for reducing the wrinkles on the skin substantially without eye irritation. In one embodiment, the topical composition contains about 0.5 to about 3.0 parts by weight of the extract which is applied topically to the target site.

The extract composition of the invention contains substantially all of the extractable components from the plant material in a concentrated form. The extract in preferred embodiments contains the extractable components in substantially the same ratio as in the original plant material. Preferably, the extract contains miroestrol, deoxymiroestrol, diadzin, puerarin, genistin, diadzein and genistein.

The extract of the invention is preferably carried out by a sequential process where the plant material is contacted in successive steps with a solvent. The solvent in each successive step is preferably an aqueous solvent containing a water miscible organic solvent in different ratios. In one embodiment, the successive solvents contain increasing amounts of the organic solvent. Each successive extraction solvent preferably increases the amount of the organic solvent by at least 5%, and typically about 5-10% by volume. In one particular embodiment, the extraction process utilized three successive extraction steps where each successive extraction liquid is an aqueous liquid containing 40%, 50% and 60% ethanol, respectively.

The various embodiments of the invention are basically attained by providing a process for producing an extract of *Pueraria candollei* var. *mirifica* Airy Shaw. & Suvat. comprising the steps of: obtaining a dry particulate of *Pueraria candollei* var. *mirifica* A Shaw. & Suvat.; contacting the particulate with an aqueous solvent including about 40% to about 60% by volume of a lower alcohol, and obtaining a liquid extraction; and drying the liquid extraction to obtain a substantially dry extract.

The advantages of the invention are further attained by providing a composition having an anti-skin wrinkling effect to the skin of a subject without irritation to the eye of the subject. The composition comprises a carrier and an effective amount of an extract of *Pueraria candollei* var. *mirifica* A Shaw. & Suvat. to reduce skin wrinkles. The extract is obtained by the process of obtaining a dry particulate of *Pueraria candollei* var. *mirifica* A Shaw. & Suvat., contacting the particulate with a first aqueous extraction liquid containing ethanol and obtaining a first liquid extract, and thereafter contacting the particulate with a second aqueous extraction liquid containing ethanol and obtaining a second liquid extract. The ethanol concentration of the second extraction liquid is greater than the ethanol concentration of the first extraction liquid. The first and second extraction liquids are combined and evaporated to dryness to obtain the extract.

The advantages of the invention are also attained by providing a process of reducing wrinkles of the skin of a subject in need thereof comprising topically applying a composition containing an effective amount of an extract of *Pueraria candollei* var. *mirifica* A Shaw. & Suvat. to the skin of a subject to reduce wrinkles of the skin, wherein the extract is obtained according to the process of the invention.

The advantages of the invention are still further attained by providing a substantially dry extract of *Pueraria candollei* var. *mirifica* A Shaw. & Suvat. obtained by the process of obtaining a dry particulate of *Pueraria candollei* var. *mirifica* A Shaw. & Suvat. and contacting the particulate with a first aqueous solvent including about 40% to about 49% by volume of a lower alcohol and obtaining a first liquid extraction.

The particulate is contacted with a second aqueous solvent including about 50% to 59% by volume of a lower alcohol and a second liquid extraction is obtained. The particulate is contacted with a third aqueous solvent including about 60% to 69% by volume of a lower alcohol and a third liquid extraction is obtained. The first, second and third liquid extractions are combined and the extractions are dried to obtain a substantially dry extract.

These and other aspects of the invention will become apparent from the following detailed description of the invention.

DETAILED DESCRIPTION OF THE INVENTION

The present invention is directed to an extract and to a process for producing an extract from *Pueraria candollei* var. *mirifica* A Shaw. & Suvat. The resulting extract is found to have all of the active compounds present in the native plant material. For example, the extract contains a concentrated mixture of the phytoestrogens in substantially the same ratio as in that are found in the plant.

A primary aspect of the invention is directed to an extraction process, the resulting extract and compositions containing the extract obtained from *Pueraria candollei* var. *mirifica* Airy Shaw. & Suvat.

The genus *Pueraria* comprises numerous members, which are widespread in Asia, Australia, Africa and North, Central and South America. Thirteen species have been taxonomically identified in Thailand, namely:

1. *Pueraria candollei* Graph. Ex. Benth
2. *Pueraria candollei* var. *mirifica* A Shaw. & Suvat.
3. *Pueraria alopecuroides* Craib
4. *Pueraria imbricata* van der Maesen sp. Nov.
5. *Pueraria lobata*
6. *Pueraria lobata* var. *ontana*
7. *Pueraria lobata* var. *thomsoni*
8. *Pueraria* var. *phaseoloides*
9. *Pueraria* var. *javanica*
10. *Pueraria* var. *subspicata*
11. *Pueraria wallichii*
12. *Pueraria rigens*
13. *Pueraria stricta*

The required species of the present invention is not "*Pueraria mirifica*" but *Pueraria candollei* var. *mirifica* A Shaw. & Suvat. While *Pueraria candollei* Graph Ex. Benth is closely related, it takes highly skilled harvesters to be able to select the correct species. *Pueraria candollei* Graph Ex. Benth does not contain Miroestrol, which is the desired constituent of the present invention. In addition, the isoflavonoid content is much lower in *Pueraria candollei* Graph Ex. Benth than in *Pueraria candollei* var. *mirifica* A Shaw. & Suvat. Collectors should avoid collecting any of the other 11 species widespread in Thailand.

The extract is obtained by a solvent extraction process from the tuberous roots of *Pueraria candollei* var. *mirifica* A Shaw. & Suvat. In one embodiment, the tuberous roots are dried and ground to a powder having a particle size that is amenable for solvent extraction. In other embodiments, the raw plant material is used without drying. The resulting powder or macerated plant material is placed in a column or filtration device and the solvent is passed through the column or filtration device. The volume of the solvent is selected in relation to the amount of the plant material being treated, and is preferably sufficient to extract substantially all of the extractable compounds from the plant material. The extraction solvent can be continuously passed through a bed of the powdered or granulated plant material. Alternatively, the extraction solvent can be contacted with the powder or granular plant material in several batches and then the batches can be combined.

In preferred embodiments, the extraction solvent containing the extracted compounds is evaporated to produce a substantially dry alcohol free extract. The solvent can be recovered for further use, if desired. Preferably, all or substantially all of the extraction solvent is evaporated to provide a substantially dry solid extract containing all of the extractable compounds, and preferably substantially all of the phytoesterols from the plant material. Preferably the resulting extract is a free flowing powder. In one preferred embodiment, the extract contains substantially all of the miroestrol, and deoxymiroestrol that were present in the native plant material and in the same proportions of the native plant material.

Preferably, the solvent is removed by an evaporation process that does not cause decomposition of the active components that are extracted from the plant material. In one embodiment, the solvent is removed under a pressure below atmospheric pressure and at a temperature that is sufficient to remove the solvent efficiently without decomposing the extracted compounds. In a preferred embodiment, the solvent is evaporated at a temperature of about 45° C.

The extraction solvent can be one or more of a number of suitable solvents as known in the art. Examples of solvents that can be used include water, ethanol, methanol, propanol, isopropanol, hexane and lower aldehydes and ketones, as well as other organic solvents as known in the art. The extraction process can use one or more solvents that can be combined to form a single solvent system. Preferably, the extraction solvent is an aqueous solvent containing about 40% to about 60% by volume of a lower alcohol, which is preferably ethanol. Alternatively, the solvents can be used separately to obtain different extracts containing a fraction of compounds that are extracted by the particular solvent. The separate extracts are then combined and the solvent evaporated to obtain the dry extract. The solvent and cosolvents are preferably miscible with each other when the extraction system contains a mixture of solvents.

In one preferred embodiment, the extraction solvent is in a water-ethanol mixture. The concentration of the ethanol in one embodiment ranges from about 40% to about 60% by volume. In other embodiments, the extraction process is carried out using successive extraction steps with an extraction solvent containing different ratios of ethanol and water. Each of the resulting extract solutions are combined and the solvent evaporated to obtain the dry extract. One embodiment of the invention uses successive extraction steps containing successively increasing amounts of ethanol. For example, the successive extraction steps use a water-ethanol mixture in a ratio of about 40% by volume ethanol to about 60% by volume ethanol in 5% increasing increments. In other embodiments, the extraction process uses three extraction steps using water-ethanol mixtures containing 40%, 50% and 60% by volume ethanol for each successive extraction step. In each of these processes, the extraction solvents are combined and evaporated to produce the dry extract. Alternatively the extraction process can be carried out in successive steps using decreasing amounts of the alcohol in the aqueous solvent.

In one preferred embodiment, the plant material is extracted with successive aqueous solvent mixtures containing at least 40% by volume of a lower alcohol and particularly ethanol. The extraction contacts the plant material with a first extraction liquid containing about 40% to about 49% of an alcohol to obtain a first liquid extract. Thereafter, the plant material is subsequently contacted with a second aqueous extraction liquid containing about 50% to 59% of an alcohol to obtain a second liquid extract. The plant material in one preferred embodiment is then contacted with a third extraction with a third extraction liquid containing about 60 to about 65% of an alcohol where the percentages are by volume. In a further embodiment, the third extraction liquid can contain about 60% to about 69% of the alcohol. The liquid extracts are then combined and reduced to dryness to obtain a powdered extract. Preferably the same alcohol is used in each of the extraction steps.

The resulting extract is preferably alcohol free and can be reduced to a free flowing powder or granular material. The powder can then be dispersed in a suitable carrier for topical or internal use. The powder can also be used to form capsules or tablets of the substantially pure extract for internal use.

In certain embodiments, the extract obtained from the Pueraria candollei var. mirifica A Shaw. & Suvat. is combined with a suitable solvent or carrier. Examples of suitable carriers include butylene glycol, propylene glycol and glycerin. Glycerin is generally preferred for topical and internal use. The carrier can contain small amounts of water. Preferably, the amount of water is sufficiently small to inhibit the precipitation of compounds that are insoluble or only marginally soluble in water and to inhibit the growth of microorganisms. In one embodiment, a topical composition is a suspension consisting essentially of glycerin and about 1.0 to 5.0% by weight of the dry powdered extract.

In preferred embodiments, the final composition contains at least about 20 mg miroestrol and deoxymiroestrol per 100 g of the composition. The composition also contains the various isoflavonoids that are present in the plant material. The isoflavonoids are preferably included in the composition to provide about 3-11 mg diadzin, about 12-30 mg puerarin, about 0.5-2 mg genistin, about 1.1 to 3.6 mg diadzein, and about 0.2 to 2 mg genistein based on 100 g of the final composition.

The extract of Pueraria candollei var. mirifica A Shaw. & Suvat. is used to produce various topical compositions for cutaneous use and oral compositions for internal use. Generally, the final composition contains about 0.5 to about 3.0 w/w of the extract. The topical compositions are suitable for use in applying to the breast to promote breast enlargement. In other embodiments, the composition is applied to the skin of a subject in need thereof to reduce the appearance of age lines and wrinkles, particularly around the eyes. The extract can be used around the eyes to reduce the signs of wrinkles without irritation of the eyes since the extract is non-irritating to the eyes. The topical compositions are generally in the form of body gels, creams and lotions.

In another embodiment, the extract of Pueraria candollei var. mirifica A Shaw. & Suvat. is administered orally to a patient in need thereof as an estrogen replacement for menopausal women. It is believed that the phytoestrogens of the extract of Pueraria candollei var. mirifica A Shaw. & Suvat. bind to the estrogen receptors with respective degrees of affinity. In this manner, the phytoestrogens from the extract of Pueraria candollei var. mirifica A Shaw. & Suvat. can reduce the effects of estrogen insufficiency in the body and provide relief to the symptoms caused by estrogen insufficiency. The consumption or internal use of the phytoestrogen present in the extract can also lower the risk of cardiovascular diseases that can result from conventional estrogen replacements. Isoflavonoids similar to those extracted from Pueraria candollei var. mirifica A Shaw. & Suvat. are known to decrease the level of LDL cholesterol and increase the level of HDL in blood. The extract of Pueraria candollei var. mirifica A Shaw. & Suvat. is administered orally to a subject in need thereof in a method to reduce the level of low density lipids (LDL) and increase the level of high density lipids (HDL) in humans.

Pueraria candollei var. mirifica A Shaw. & Suvat. contains different types of phytoestrogens, which may be broadly classified into three main groups:

1. The miroestrol and deoxymiroestrol are comparatively potent phytoestrogens unique to Pueraria candollei var. mirifica A Shaw. & Suvat., their structural configuration is very close to the structural configuration of estradiol-17β as shown by the following formulas.

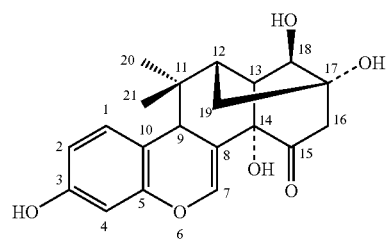

Miroestrol

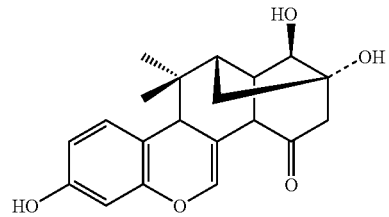

Deoxymiroestrol

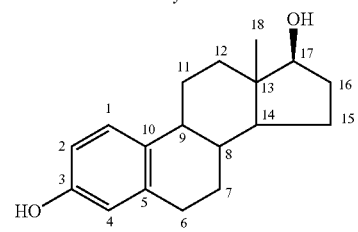

Estradiol-17B

2. The isoflavonoid compounds of Pueraria candollei var. mirifica A Shaw. & Suvat., which comprises daidzin and daidzein, genistin and genistein, and puerarin have the formulas:

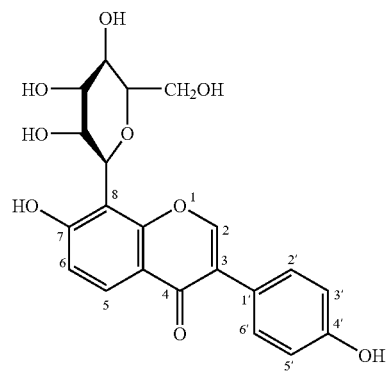

Puerarin
MW 416

-continued

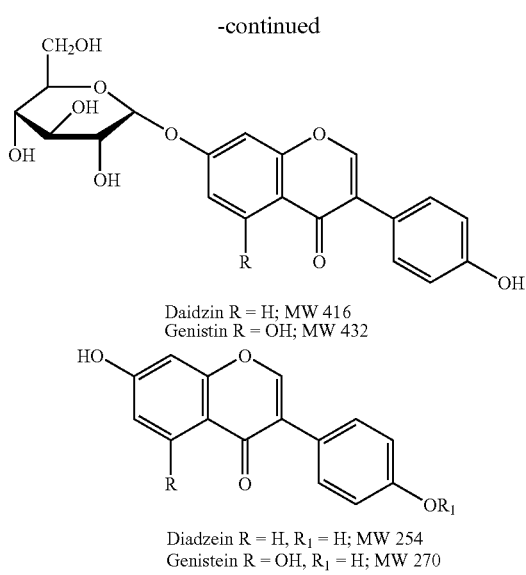

Daidzin R = H; MW 416
Genistin R = OH; MW 432

Diadzein R = H, $R_1$ = H; MW 254
Genistein R = OH, $R_1$ = H; MW 270

3. The coumestan compound comprises coumestrol.

This wide variety of phytoestrogenic compounds belonging to different groups and present side by side in a single plant makes *Pueraria candollei* var. *mirifica* A Shaw. & Suvat. a very suitable herb for hormone supplements to treat the decline in the natural hormones in women over 45 years of age. Taking estrogenic hormones has been shown to be carcinogenic in some case studies. On the other hand, taking phytoestrogens proved to be anti-carcinogenic or at least delay carcinogenic manifestations. A considerable amount of data has been accumulated proving that phytoestrogens exhibit an inhibitory effect against mammary tumorigenesis, prostate-related cancer and bladder cancer.

Phytoestrogens also exhibit favorable effects other than the dramatic results of protection against certain types of cancer. In other words, as a result of the decrease in the level of estrogenic hormones, the body's systems and their functions begin to decelerate and the immune system weakens. Accordingly, menopausal women will usually experience both psychological and physiological changes. Psychological changes range from anxiety, tension and nervousness to chronic depression, whereas the physiological changes include hot flashes, fatigue and insomnia, to more severe conditions such as bone loss, balding and degeneration of the reproductive area.

The structure of miroestrol is not a steroidal hormone but is a 21 carbon compound with a 6-membered ring instead of the 5-membered ring of estradiol-17β. The similarity between miroestrol and estradiol-17β is in the size of the 4-ring molecule. The aromatic ring with the phenolic hydroxyl group at position 3 are present in miroestrol and estradiol-17β. The β-hydroxyl group at position 18 in miroestrol corresponds to the 17β-hydroxyl group of estradiol-17β and the β-hydroxyl group in the 17 position of estriol. The 17α-hydroxyl group of miroestrol corresponds to the 16α-hydroxyl group of estriol. Miroestrol is a unique phytoestrogen that is very similar to estriol while being non-hormonal and non-steroidal. The unique estrogenic effect of *Pueraria candollei* var. *mirifica* A Shaw. & Suvat. is a result of the similarity of the standardized liquid product of the invention. While being the form of choice for formulating products for cutaneous applications, it is also very suitable for internal use providing a superior bioavailability. The preferred vehicle is glycerol as the only solvent, carrier or vehicle. However, since many people find the solid dosage form practical for administration and accurate dosing, a powdered extract is produced which can be easily formulated into tablets and capsules.

The powdered tuberous root of *Pueraria candollei* var. *mirifica* A Shaw. & Suvat. differs in analysis from one season to another and is affected considerably by the atmospheric conditions. In particular, the amount of rain in the region of the world where the plant is indigenous is a significant factor in determining the amount of each of the phytoestrogens in the plant material. Therefore, for internal therapeutic use, the production of a standardized powdered extract is preferred. No such product has been produced so far for the market.

The same identification and extraction procedure is followed for the preparation of the standardized liquid. The extract is analyzed chemically and the percentage of solids determined. The calculated amount of diluent is added. Such diluent may be maltodextrin or Capsul™, then USP purified water is added to bring the total solids to about 40% which is a suitable concentration for spray-drying. The optimum spray-drying condition for *Pueraria candollei* var. *mirifica* A Shaw. & Suvat. to obtain a powdered extract is 390-400° F. inlet temperature and 190-200° F. outlet temperature (regulated by the rate of flow of the feeding liquid). During spray-drying, the relative humidity is kept between 40-50%. In one embodiment of the invention a spray dried powdered extract is obtained by preparing a mixture of a liquid carrier containing about 20% to about 50% and preferably about 35% to about 45% solids of the extract from the plant material and spray drying. The resulting spray dried extract is a dry free flowing powder.

The standardized powdered extract is adjusted to comply with the adjusted product specification which is identical to the concentrations of the liquid extract product. Preferably, each 100 g of the powdered extract contains ≧20 mg miroestrol (deoxymiroestrol), about 3-11 mg daidzin; about 12-30 mg puerarin; about 0.5-2 mg genistin; about 1.1-3 mg daidzein; and about 0.2-2 genistein. The recommended dose of the product for internal use is 80 mg of the extract 1 to 2 times/day.

The stability of the constituents was monitored by HPLC before and after spray-drying. No decomposition or degradation could be noticed (neither new peaks, nor disappearance nor reduction of any peak, nor the appearance of new shoulders). This provides reasonable assurance that a constituent, standardized and effective product is produced. Toxicity tests using a mutagenicity assay have shown the extract is negative for *Staphylococcus Aureus, Salmonella typhimurium* and *E. coli*.

EXAMPLE 1

This example evaluates the toxicity and irritancy of the extract. The chick embryo has been used extensively in toxicology. The chorioallantoic membrane (CAM) of the chick embryo is a complete tissue with organoid elements from all germ cell layers. The chorionic epithelium is ectodermal and the allantoic epithelium is endodermal. The mesoderm located between these epithelia is a complete connective tissue including arteries, capillaries, veins and lymphatic vessels. The CAM responds to injury with a complete inflammatory reaction, comparable to that induced in the rabbit eye test. It is technically easy to study, and is without nerves to sense pain.

Fresh, fertile, White Leghorn eggs were obtained from Avian Services in Frenchtown, N.J. They were stored at this facility for up to seven (7) days, at 13° C., before being incubated. For incubation, the eggs were placed on their sides, in a Kuhl incubator. The incubator is such that the eggs are automatically rotated once every hour. The temperature was controlled at 99° F. (±1°) with a relative humidity of 60-70% for the ten (10) days of incubation. On day eight (8) the eggs were turned so that the acutely angled end faced down.

On day ten (10), each egg was removed from the incubator and placed in a Plexiglas work enclosure. This enclosure had been preheated and humidified so that its environment approached that of the incubator. A cut was made in the larger end of each egg, where the air sack is located. A Dremel® Moto-Flex Tool (model 232-5) equipped with a Dremel® Cut-Off Wheel (No. 409) was used to make each cut. Forceps were then used to remove the shell down to the shell-membrane junction. The inner egg membrane was then hydrated with a warm, physiological saline solution. The saline was removed after a two (2) to five (5) minute exposure. Utilizing pointed forceps, the inner egg membrane was then carefully removed to reveal the CAM.

The test or reference article, at a dosage of three-tenths of one milliliter (0.3 ml) of a liquid or three-tenths of one gram (0.3 g) of a solid was then administered to each of four (4) CAM's. Twenty seconds later, the test or control article was rinsed from each CAM with five (5) milliliters of physiological saline. All CAM's were observed immediately prior to test article administration and at 30 seconds, two (2) and five (5) minutes after exposure to the test article. The reactions of the CAM, the blood vessels, including the capillaries, and the albumin were examined and scored for irritant effects as detailed below:

| | Score Time (min.) | | |
|---|---|---|---|
| Effect | 0.5 | 2 | 5 |
| Hyperemia | 5 | 3 | 1 |
| Minimal Hemorrhage ("Feathering") | 7 | 5 | 3 |
| Hemorrhage (Obvious Leakage) | 9 | 7 | 5 |
| Coagulation and/or Thrombosis | 11 | 9 | 7 |

The numerical, time dependent scores were totaled for each CAM. Each reaction type can be recorded only once for each CAM, therefore the maximum score per CAM is 32. The mean score was determined for all CAM's similarly tested.

| Test Article (%) | CAM# | Scores@ 0.5 min. | 2 min. | 5 min. | Total |
|---|---|---|---|---|---|
| PM, PE, Product Code: 4523, Lot Number: 031615 Date: Mar. 1, 2004 (2.5%) | 1 | 0 | 0 | 1 | 1 |
| | 2 | 0 | 3 | 0 | 3 |
| | 3 | 0 | 3 | 0 | 3 |
| | 4 | 0 | 3 | 0 | 3 |
| | | | | Average: | 2.50 |

| Reference Article (%) | CAM# | Scores@ 0.5 min. | 2 min. | 5 min. | Total |
|---|---|---|---|---|---|
| Johnson's Baby Shampoo (50%) | 1 | 5 7 | 0 | 0 | 12 |
| | 2 | 5 7 | 0 | 0 | 12 |
| | 3 | 0 | 3 5 | 0 | 8 |
| | 4 | 5 7 | 0 | 0 | 12 |
| | | | | Average: | 11.00 |

| Reference Article (%) | CAM# | Scores@ 0.5 min. | 2 min. | 5 min. | Total |
|---|---|---|---|---|---|
| Head & Shoulders Shampoo (50%) | 1 | 5 7 | 0 | 5 7 | 24 |
| | 2 | 5 7 | 0 | 5 7 | 24 |
| | 3 | 5 7 | 7 | 0 | 19 |
| | 4 | 5 7 | 0 | 5 | 17 |
| | | | | Average: | 21.00 |

Each article was then classified as indicated in the following:

| Mean Score | Irritation Potential |
|---|---|
| 0.0-4.9 | Practically none |
| 5.0-9.9 | Slight |
| 10.0-14.9 | Moderate |
| 15.0-32.0 | Severe |

The irritation potential of this test article was at 5%. Previous studies have shown that the CAM of the hen's egg is more sensitive to liquid irritants than is the rabbit eye. Therefore, dilutions of the liquid test and reference articles were used. The Johnson's reference product has historically been categorized as being moderately irritating, eliciting scores approaching 10, at 24 hours, when dosed at 100% and tested using the Draize ocular irritation methodologies. The Head & Shoulder's reference product has historically been categorized as being severely irritating, eliciting scores approaching 30, at 24 hours, when dosed at 100% and tested using the Draize ocular irritation methodologies. Under the conditions of this test, the results indicate that the extract exhibited practically no ocular irritation potential in vivo.

While various embodiments of the invention have been chosen to illustrate the invention, it will be understood by those skilled in the art that various changes and modifications can be made without departing from the scope of the invention as defined in the pending claims.

What is claimed is:

1. A process for producing an extract of *Pueraria candollei* var. *mirifica* Airy Shaw. & Suvat. comprising the steps of:
    obtaining a dry particulate plant material of *Pueraria candollei* var. *mirifica* A Shaw. & Suvat.;
    contacting said particulate with a first aqueous ethanol extraction solvent consisting essentially of a mixture of water and about 40% to 60% by volume ethanol, and obtaining a first liquid extract;
    contacting the first extracted particulate with at least one second aqueous ethanol extraction solvent consisting essentially of water 60% to 69% by volume ethanol to obtain a second liquid extract;

combining the first and second liquid extracts and drying the liquid extracts to obtain a substantially dry extract, wherein said dry extract comprises at least 20 mg miroestrol and deoxymiroestrol, about 3-11 mg daidzin, about 12-30 mg puerarin, about 0.5-2.0 mg genistin, about 1.1-3.6 mg daidzein, and about 0.2-2 mg genistein based on 100 g of said extract.

2. The process of claim 1, further comprising contacting the first extracted particulate with a third aqueous solvent containing about 40% to about 49% by volume ethanol and obtaining a third liquid extract; and
combining said third liquid extract with said first and second liquid extracts and drying said liquid extracts to a dryness to obtain said dry extract.

3. The process of claim 2, further comprising contacting said particulate with an aqueous ethanol liquid containing about 50% to 59% by volume ethanol to obtain a fourth liquid extract;
combining said fourth liquid extract with said first, second and third liquid extracts; and
drying said liquid extracts to obtain said extract.

4. The dry extract obtained by the process of claim 1.

5. A process for producing an extract from *Pueraria candollei* var. *mirifica* A Shaw. & Suvat. containing miroestrol, deoxymiroestrol, diadzin, puerarin, genistin, diadzein and genistein, the process comprising the steps of:
contacting a dry particulate plant material of *Pueraria candollei* var. *mirifica* A Shaw. & Suvat. with at least one first ethanol extraction solvent containing about 40% to about 69% by volume ethanol and obtaining a first extraction liquid;
contacting the first extracted particulate plant material with a second ethanol extraction solvent and obtaining a second liquid extract, wherein said second aqueous ethanol solvent has an ethanol concentration greater than said first aqueous solvent;
contacting the second extracted particulate plant material with a third ethanol extraction solvent obtaining a third liquid extract, wherein the ethanol content of the third ethanol extraction solvent is different from the ethanol content of the first and second ethanol extraction solvents; and
combining said first and second liquid extracts and drying said combined liquid extracts to obtain a substantially dry extract comprising at least 20 mg miroestrol and deoxymiroestrol, about 3-11 mg diadzin, about 12-30 mg puerarin, about 0.5-2.0 mg genistin, about 1.1-3.6 mg diadzein, and about 0.2-2 mg genistein based on said extract.

6. The process of claim 5, wherein said extraction solvents consist essentially of water and ethanol.

7. The process of claim 6, further comprising contacting the first extracted particulate plant material with an ethanol extraction solvent consisting essentially of water and about 50% to 59% by volume of ethanol to obtain a liquid extract, combining the liquid extracts and drying to obtain said dry extract.

8. The process of claim 7, the process comprising:
contacting the second extracted particulate with an ethanol extraction solvent containing about 60% to about 69% by volume of ethanol to obtain a liquid extract; and
combining said liquid extracts and drying said extracts to obtain said substantially dry extract.

9. The process of claim 1, wherein said process comprises placing said particulate in a column and passing said ethanol extraction solvents sequentially through said column to obtain said liquid extracts.

10. The process of claim 1, wherein said dry extract contains said miroestrol, deoxymiroestrol, daidzin, puerarin, genistin, daidzein, and genistein in substantially the same proportions as the particulate native plant material.

11. A process for producing an extract of *Pueraria candollei* var. *mirifica* Airy Shaw. & Suvat. comprising the steps of:
obtaining a dry particulate plant material of *Pueraria candollei* var. *mirifica* A Shaw. & Suvat.;
contacting said particulate plant material with an extraction solvent containing about 40% to 60% by volume ethanol, and obtaining a first liquid extract;
contacting the first extracted particulate plant material with an extraction solvent containing 60% to 69% by volume ethanol to obtain a second liquid extract;
contacting the second extracted particulate plant material with an extraction solvent containing ethanol and obtaining a third liquid extract and where said third extraction solvent has an ethanol content greater than said first extraction solvent; and
combining the liquid extracts, and drying the liquid extracts to obtain a substantially dry extract comprising at least 20 mg miroestrol and deoxymiroestrol, about 3-11 mg daidzin, about 12-30 mg puerarin, about 0.5-2.0 mg genistin, about 1.1-3.6 mg daidzein, and about 0.2-2 mg genistein based on 100 g of said extract, and where said daidzin, puerarin, genistin, daidzein and genistein in the dry extract are present in substantially the same proportions as said dry particulate plant material.

12. The process of claim 11, wherein said extraction solvent in the first extraction step contains about 40% to about 49% by volume ethanol.

13. A process of reducing wrinkles of the skin of a subject in need thereof comprising:
topically applying a composition containing an effective amount of an extract of *Pueraria candollei* var. *mirifica* A Shaw. & Suvat. to the skin of the subject to reduce wrinkles of the skin, wherein said extract is obtained according to the process of claim 1.

14. The process of claim 13, comprising applying said composition to the skin around the eyes of said subject to reduce wrinkles around the eye without irritation to the eye.

15. The process of claim 13, wherein said composition contains about 0.5 to about 3 parts by weight of said extract.

16. A process for producing an extract of *Pueraria candollei* var. *mirifica* Airy Shaw. & Suvat. comprising the steps of:
obtaining a dry particulate plant material of *Pueraria candollei* var. *mirifica* A Shaw. & Suvat.;
contacting said particulate with a first aqueous extraction solvent containing about 40% to 49% by volume ethanol and obtaining a first extraction liquid;
contacting the first extracted particulate plant material with a second aqueous extraction solvent containing about 50% to 59% by volume ethanol and obtaining a second extraction liquid;
contacting the second extracted particulate plant material with a third aqueous extraction solvent containing 60% to 65% ethanol to obtain a third extraction liquid;
combining the first, second and third extraction liquids and drying the extraction liquids to obtain a dry extract comprising about 3-11 mg daidzin, about 12-30 mg puerarin, about 0.5-2.0 mg genistin, about 1.1-3.6 mg daidzein, and about 0.2-2 mg genistein based on 100 g of said dry extract.

17. A substantially dry extract of *Pueraria candollei* var. *mirifica* A Shaw. & Suvat. containing at least 20 mg miroestrol and deoxymiroestrol, about 3-11 mg daidzin, about 12-30 mg puerarin, about 0.5-2.0 mg genistin, about 1.1-3.6 mg daidzein, and about 0.2-2 mg genistein based on 100 g of said extract, obtained by the process of obtaining a dry particulate of *Pueraria candollei* var. *mirifica* A Shaw. & Suvat.;

contacting said particulate with a first aqueous solvent including about 40% to about 49% by volume of a lower alcohol and obtaining a first liquid extract;

contacting the first extracted particulate with a second aqueous solvent including about 50 to 59% by volume of a lower alcohol and obtaining a second liquid extract;

contacting the second extracted particulate with a third aqueous solvent including about 60 to 65% by volume of a lower alcohol and obtaining a third liquid extract; and combining said first, second and third liquid extracts and drying said extracts to obtain a substantially dry extract, said extract comprising at least 20 mg miroestrol and deoxymiroestrol per 100 g of said extract.

* * * * *